US006235949B1

(12) United States Patent
Garcia et al.

(10) Patent No.: US 6,235,949 B1
(45) Date of Patent: *May 22, 2001

(54) PROCESS FOR THE PREPARATION OF HALOGENATED DERIVATIVES AND LEWIS ACID BASE CATALYSTS THEREOF

(75) Inventors: Herve Garcia, Saint Fons; Laurent Gilbert, Lyons; Serge Ratton, Saint Germain en Laye; Christophe Rochin, Lyons, all of (FR)

(73) Assignee: Rhodia Chimie, Courbevoie (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/814,027

(22) Filed: Mar. 10, 1997

Related U.S. Application Data

(63) Continuation of application No. 08/319,082, filed on Oct. 6, 1994, now abandoned, which is a continuation of application No. 08/121,247, filed on Sep. 15, 1993, now abandoned, which is a continuation of application No. 07/860,215, filed on Mar. 27, 1992, now abandoned, which is a continuation of application No. 07/609,512, filed on Nov. 6, 1990, now abandoned.

(30) Foreign Application Priority Data

| Nov. 6, 1989 | (FR) | 89 14528 |
|---|---|---|
| Nov. 6, 1989 | (FR) | 89 14529 |
| Nov. 6, 1989 | (FR) | 89 14532 |

(51) Int. Cl.$^7$ ............ C07C 19/08; C07C 43/02; C07C 309/00; C07C 67/02
(52) U.S. Cl. ............ 570/142; 570/201; 568/656; 562/83; 562/125; 562/493; 560/254
(58) Field of Search ............ 570/142, 201; 568/656; 562/493, 83, 125; 560/254

(56) References Cited

U.S. PATENT DOCUMENTS

| 3,270,069 | * | 8/1966 | Olah | 570/142 |
|---|---|---|---|---|
| 3,283,018 | * | 11/1966 | Christe et al. | 570/142 |
| 4,620,040 | * | 10/1986 | Alsop | 568/656 |
| 4,847,442 | * | 7/1989 | Nalelwajek | 570/142 |

FOREIGN PATENT DOCUMENTS

| 1582427 | * | 1/1981 | (GB) | 570/142 |

* cited by examiner

*Primary Examiner*—Alan Siegel
(74) *Attorney, Agent, or Firm*—Finnegan, Henderson, Farabow, Garrett & Dunner L.L.P.

(57) ABSTRACT

A process for the preparation of halide compounds, preferably aryl halides, by contacting a gaseous mixture of hydrohalic acid and a compound selected from an aryl halogen formate, an aryl carbonate and equivalents thereof with a Lewis acid catalyst.

32 Claims, 1 Drawing Sheet

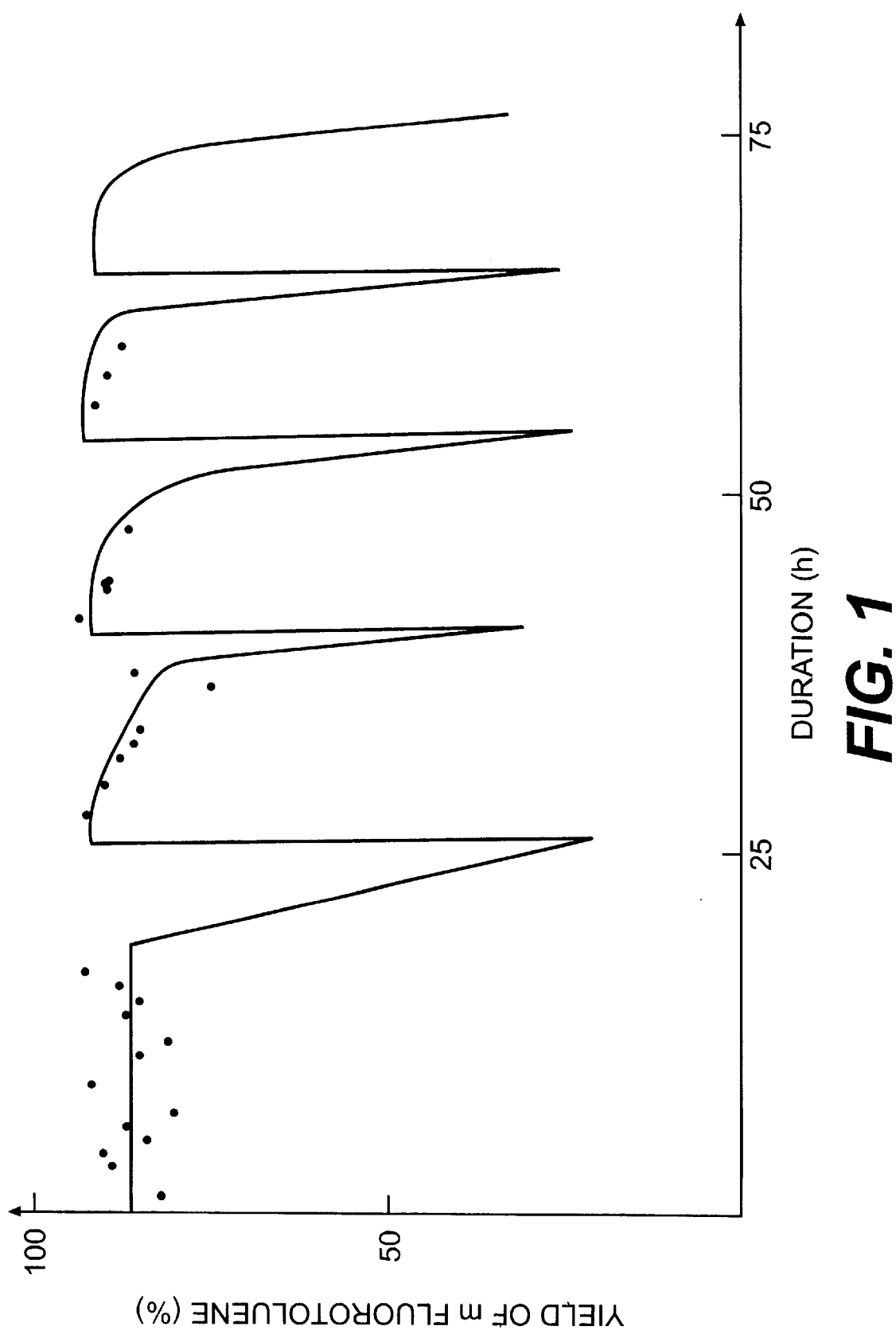

PROCESS FOR THE PREPARATION OF HALOGENATED DERIVATIVES AND LEWIS ACID BASE CATALYSTS THEREOF

This application is a continuation, of application Ser. No. 08/319,082 filed Oct. 6, 1994, now abandoned, which was a continuation of prior application Ser. No. 08/121,247 filed Sept. 15, 1993, abandoned, which was a continuation of prior application Ser. No. 07/860,215 filed Mar. 27, 1992, abandoned, which was a continuation of prior application Ser. No. 07/609,512 filed Nov. 6, 1990, abandoned.

The present invention relates to a process for the preparation of halogenated derivatives, preferably halogenated aromatic derivatives. More specifically, it relates to the preparation of aromatic derivatives that have a halogen atom attached directly to the aromatic ring. More specifically still, it relates to the preparation of fluorobenzenes.

It has been known for quite some time, e.g., from the teachings of U.S. Pat. No. 4,075,252, that fluorobenzene can be prepared from anilines by a diazotization reaction or by using a triazene intermediary and decomposing triazene or diazonium salt in hydrofluoric acid. These prior art techniques always require a two-step process. The process may be performed continuously, e.g., in accordance with European Patent EP 205,019, but still requires a step in which the azonium salt is formed and a step in which it is decomposed.

The original amines are costly compounds that are indispensable in such a process and considerably increase the ultimate cost of the fluorobenzene produced.

British Patent 1,582,427 discloses the preparation of fluorobenzene through contact, at approximately 200° C., between a phenyl and a hydrofluoric acid solution containing a Lewis acid in a quantity of between 0.5% and 25% by weight, computed with respect to the quantity of hydrofluoric acid used. In reactions of six hours in duration the output of fluorobenzene is always less than 25%.

European Patent 118,247 describes a process for preparing fluorobenzene by passing a fluoroformic acid ester over platinated alumina at a temperature of from 200°–600° C. This process, which is performed in gas phase with a fluorobenzene output that is claimed to be as high as 60%, was treated more thoroughly in a later publication (Ashton, D. P. et al., "The Preparation of Fluoroarenes By The Catalytic Decarboxilation of Aryl Flouro Formates," Journal of Flourene Chemistry, 27, 1985, 263 and 274). It suffers from a number of disadvantages, including the cost of the reagent and production of large quantities of numerous by-products. Furthermore, the catalyst is poisoned very quickly and the necessary regeneration makes the process too costly to contemplate its use on an industrial scale. The explanation given for the poisoning of the catalyst is its degradation under the effect of hydrofluoric acid.

Consequently, one of the purposes of the present invention is to provide a process for preparing aryl halides that will eliminate or lengthen the regeneration cycles. A further purpose of the invention is to provide a separate process that uses less costly raw materials.

BRIEF DESCRIPTION OF THE DRAWINGS

FIG. 1 graphically depicts the yield vs. time results for Example 17.

The aforementioned purposes and others that will appear hereinbelow are achieved by means of a process for preparing a halide compound, preferably an aryl halide that includes a reactive step in which a gaseous mixture containing hydrohalic acid and at least one of a halogen formate, preferably an aryl halogen formate, a carbonate, preferably a halogen carbonate, and more preferably an aryl carbonate and equivalents, preferably halogenated equivalents thereof is reacted in the presence of a Lewis acid-based catalyst (hereinafter, a Lewis acid catalyst) for a time sufficient to form the halide compound. The halide compound is formed by removing the substituent or radical in contact with the aromatic ring and bonding a halide directly to the aromatic ring. Equivalents include any compound capable of use in the instant invention for forming a halide compound, preferably an aryl halide. These formates, carbonates and equivalents are generally represented by a compound having a radical of the formula (I)

$$-O-CY-A \qquad (I)$$

wherein Y represents a chalcogen (an element from group VIa of the periodic table), preferably a light chalcogen which includes S or O, more preferably oxygen, or two halogen atoms, preferably the same halogen atoms;

wherein A represents a halogen or an $-OR'_2$ group in which $R'_2$ represents an aliphatic radical containing 1 to 4 carbon atoms, which may be halogenated; or an aromatic radical, which may be substituted by an alkyl group containing 1 to 4 carbon atoms, an alkylthio group containing 1 to 4 carbon atoms, an alkoxy radical containing 1 to 4 carbon atoms, hydroxyl, halogen, or at least one nitro group; or an $-NR'''_2R''_2$ group in which $R'''_2$ represents:

an aliphatic radical containing 1 to 4 carbon atoms, preferably halogenated; or an aromatic radical preferably substituted by an alkyl containing 1 to 4 carbon atoms, alkoxy containing 1 to 4 carbon atoms, nitro, halogen or hydroxyl group;

in which $R''_2$ represents:

a hydrogen; an aliphatic radical containing 1 to 4 carbon atoms, preferably hydrogenated; or an aromatic radical preferably substituted by an alkyl containing 1 to 4 carbon atoms, alkoxy containing 1 to 4 carbon atoms, nitro, halogen or hydroxyl group.

Generally, the molar ratio of the hydrohalic acid to the substrate (i.e. a compound having a radical of formula (I)) is preferably at least 1:1, more preferably between 5:1 and 1,000:1, and more preferably between 10:1 and 1,000:1. The molar ratio may be as low as $10^{-1}:1$ if, for example, there is no halogen to be brought to the substrate such as by exchange with gaseous hydrogen halogenide.

The molar ratio of hydrohalic acid to the substrate is preferably calculated based upon the stoichiometric quantity of halogen required to effect complete halogen exchange. The molar ratio is preferably in excess of the stoichiometric quantity required. Thus, in the case of trichloromethoxybenzene, the lower limit for the molar ratio preferably becomes about 7:1. The amount of hydrohalic acid preferably used is calculated as twice the number of moles of substitutable halogen present in the substrate (i.e. 3), plus excess, for example 1 (e.g. (2×3)+1).

Advantageously, the temperature is preferably between 200° and 800° C. and more preferably between 200° and 500° C. Additional optimization within the above ranges is contemplated but good results are achieved with the stated values.

Generally, the yield of halide compound (e.g. aryl halide) is greater than 0.5%, preferably greater than 2.5%, and more preferably greater than 30%.

In addition to the reagents, the gaseous mixture may contain a gas that is inert with respect to the reaction substances and the catalyst. This gas may play the role of a vector gas or of a diluting agent when the molecules of the compounds of formula (I) are sufficiently reactive to react with each other or with the aryl halide produced by the reaction. The gaseous mixture is preferably at a total pressure of between $10^{-2}$ and 20 MPa, more preferably between $10^{-1}$ and 20 MPa, and still most preferably between $10^{-1}$ and 2 MPa.

It is desirable that the reaction mixture be anhydrous, i.e., that the molar water content be preferably no more than 10%, and more preferably 1%, of the substrate, preferably the aryl substrate. The anhydrous nature of the gaseous reaction mixture is limited by the water content of commercially available hydrohalic acid, preferably hydrofluoric acid, which is labelled as anhydrous.

Lewis acids as herein defined are understood to mean compounds which accept an electron pair. Paradigms of these compounds are found in "Friedel-Crafts And Related Reactions" by G. A. Olah, 1963, Vol.II, pages 191–197, 201, 202 and 225–291 which is herein specifically incorporated by reference.

Advantageously, the catalyst may contain at least one chemical substance selected from (a) the transition elements (the element having subshell d filled, i.e., elements of column IVa to IIb, the metallic elements of column IIIa, IVb and Vb, wherein the elements of columns IVb and Vb are preferably from the third period and more preferably from the fourth period), preferably the transition metals are the metallic elements of Columns III, IVb and Vb; (b) germanium and silicon in elementary form, and (c) low ranking alkaline-earth elements up to and including magnesium. Appropriate chemical substances are utilized as chalcogenides (preferably oxides), halogenides, carbonates, sulfates, phosphates, and their decomposable organic salts, alloys and mixtures thereof. The oxy-halogenides are members of this group.

Generally, suitable catalyst compounds include any derivative or mixture, which when subjected to the reaction mixture, produces at least some halide, preferably fluoride. These fluorides may include chalcogeno-fluorides, which may be mixed and which may include other elements, provided the Lewis acid character is maintained.

Halides, oxyhalides, and substances that are wholly or partially converted to halides and oxyhalides, preferably fluorides and oxyfluorides, under the effect of gaseous hydrohalic acid, can yield particularly satisfactory results. With the Lewis acids derived from column IIIa elements, the preferred rare earth elements are scandium, actinium, thorium and uranium. The preferred transition elements are Cr, Fe, Mo, W, Ag, Cu, Zn, Ti, Co, Ni, Ta, Nb, V, Au and Re. The more preferred transition elements are chromium, nickel, cobalt, iron and/or molybdenum.

The substances that are wholly or partially converted to halides or oxyhalides may also include metallic alloy steel, preferably austentic. For example steel containing chromium, nickel or possibly molybdenum may be used. The substance may also be Hastelloy C 276, a steel alloy. When using Hastelloy C 276 steel the volume conversion rates can be weak. When the substance is a metallic alloy, it should be capable of corroding to form a Lewis acid at its surface. Additional preferred elements include tin, germanium, lead, the elements of column IIIb (preferably Al, Ga, In) and antimony. Reference is made to the French classification (cf. Bull. Soc. Chim. No. 1, January 1966). This substance may also be a zeolite, preferably type Y, i.e., with a very low Si:Al ratio.

It is possible, indeed advantageous, to subject the catalyst prior to use, to the effect of hydrohalic acid under the conditions of the procedure disclosed by the present invention. From among the alloys, those that give the best results are those that exhibit corrosion after their contact with hydrohalic acid.

Derivatives which exhibit catalytic properties may be used in their ordinary form or they may be supported according to standard techniques applicable to solid catalysis of a gaseous reaction. It is apparent that when using catalyst compounds which are in fluid form at the temperature of operation, it is highly desirable to support them.

Operating in accordance with the invention, it has been possible to show that metallic catalysts, including those based on the chemical substances mentioned hereinabove, result in rates of conversion of compounds having a radical of the formula (I), preferably aryl halogen formates and aryl carbonates, into the corresponding fluoride in excess of 90%.

Furthermore, there is little or no need to regenerate the catalyst. Where regeneration is appropriate, regeneration can be quickly and easily carried out by passing a stream of oxygen-rich gas over the catalyst, at a temperature close to or higher than the operating temperature.

It should be noted that the contact time, defined by $T_f=m/F$ (where m is the mass of catalyst and F is the flow rate of gas at the reaction temperature, expressed in $cm^3$ per second), is generally between $10^{-3}$ and $100$ g×s/$cm^3$ which falls within the range of relative rapid industrial reactions. Of course, the contact time is specific to the texture and nature of the catalyst.

A large number of halogenated aromatic compounds may be prepared in this manner. The limitations essentially concern (i) the stability of the aromatic ring of the substrate at the chosen temperature, and (ii) the saturating vapor pressure of the original compound having a radical of the formula (I), preferably halogen formate or carbonate. The donor substituents on the aromatic ring favor the completion of the reaction to a greater extent than the acceptors discourage it.

At the temperatures at which the process is carried out, the latter compounds are at a saturating vapor pressure preferably of at least $10^{-3}$, and more preferably $10^{-2}$ MPa. In addition, it is highly preferred that the kinetic energy of decomposition of the halogen formed be at least equal to that involved in its formation.

When the rate of decomposition is high, even if it meets the above constraint, it is preferable to quench the reaction mixture immediately following contact with the catalyst.

Preferred aryl halogen formates, aryl carbonates and equivalents thereof are compounds of the formula (II):

$(R_1)_n$—Ar—O—CY—A  (II)

wherein Y preferably represents a chalcogen, preferably a light chalcogen which includes S or O, more preferably oxygen or two halogen atoms, preferably the same halogen atoms;

Ar represents an aromatic radical, preferably a monocyclic, polycyclic or heterocyclic radical or a vinyl;

radicals $R_1$, which may be similar or different, represent: an electron attracting unit, preferably a halogen, nitro and/or cyano unit; a —Z—$R_2$ group, in which Z may be a single bond, an oxygen atom, a sulfur atom, or the groups —$NR_3$—, —Co—, —OCO—, —COO—, —SO—, —$SO_2$—, or —$SO_3$—;

$R_2$ represents a hydrogen atom or an alkyl, an acyl or an aryl radical having at least 8 carbon atoms, and where $R_3$ may be defined the same as $R_2$ or form a nitrogenous heterocycle with $R_2$ and the nitrogen atom that carries it;

n represents the number of substituents and is equal to 0 or a whole number that is no greater than the number of substitutable positions on the aromatic ring;

A represents a halogen, or an —$OR'_2$— group in which $R'_2$ represents an aliphatic radical containing 1 to 4 carbon atoms which may be halogenated, or an aromatic radical (which may be substituted by an alkyl group containing 1 to 4 carbon atoms, an alkylthio group containing 1 to 4 carbon atoms, an alkoxy radical containing 1 to 4 carbon atoms, hydroxyl, halogen, or at least one nitro group). Preferably $R'_2$ is $(R_1)_n$—Ar—O—. The vicinal groups $R_1$ may be linked to form a heterocyclic or other ring. A may also represent an —$NR'''_2R''_2$ group in which $R'''_2$ represents:

an aliphatic radical containing 1 to 4 carbon atoms, preferably halogenated; or an aromatic radical preferably substituted by an alkyl containing 1 to 4 carbon atoms, an alkoxy containing 1 to 4 carbon atoms, nitro, halogen or a hydroxyl group;

in which $R''_2$ represents:

a hydrogen; an aliphatic radical containing 1 to 4 carbon atoms, preferably hydrogenated; or an aromatic radical preferably substituted by an alkyl containing 1 to 4 carbon atoms, an alkoxy containing 1 to 4 carbon atoms, nitro, halogen or hydroxyl group.

The alkyl groups (as defined in Duvals Dictionnaire de Lachimie, Presses Scientifiques Internationnale, 6th Ed., Paris, 1959) may be (i) straight or branched aliphatic residues having at least 6 carbon atoms, or (ii) aryl aliphatic residues. They may be at least partially substituted preferably by halogens, and include the radicals derived from perfluoroalkanes.

The number of the substitutable position is easily determined using simple rules known to one of ordinary skill in the art. For example, when Ar=phenyl n≦5

Ar=pyridyl n≦4

Ar=naphthyl n≦7

Ar=quinolyl n≦6

It should be noted that the reaction is also applicable to compounds in which Ar is replaced by a vinyl radical with n≦3.

The total number of carbon atoms in the compound of Formula (II) is preferably no greater than 50 and more preferably no greater than 30.

Preferably in Formula (II), Ar represents a monocyclic aromatic radical and n is no greater than 3.

Even more preferable among the compounds of Formula (II) are those in which $R'_2$ is a methyl group or a nitro-group, or those in which $R_1$ is a halogen group and n is equal to 1.

Also preferred among the compounds of Formula (II) are those in which A is a halogen selected from among fluorine, chlorine or bromine, or a —$OR'_2$ group in which $R'_2$ represents a group with the formula: —Ar—$(R_1)_n$. More specifically, fluorine is less reactive, and bromine more reactive; the best cost/reactivity compromise is chlorine, with bromine being reserved for the most difficult syntheses.

With bromoformate, the ratio of hydrohalic acid to halogen formate is preferably on the high side of the range as specified above.

One of the advantages of the process is the ability to process reaction mixtures containing a plurality of compounds having a radical of the formula (I), for example, a mixture containing both aryl carbonate and aryl halogen formate.

The raw materials preferred for use with the invention are substituted or unsubstituted phenylfluoroformate, substituted or unsubstituted phenylchloroformate, or substituted or unsubstituted diphenylcarbonate, with symmetrical diphenylcarbonate being preferable.

In situ fabrication of compounds having a radical of the formula (I) can be used, particularly carbonates or halogen formates using carbonic acid halogenides (e.g., phosgene), or their derivatives (e.g., polyphosgene) on the corresponding phenols are also within the scope of the invention.

Similarly, producing dihalides or even polyhalides from halogen formate or carbonate derived from di- or polyphenols is also within the scope of the present invention.

Despite the highly specific nature of the fluorine atom of the fluoride, it has been possible to synthesize other halides in the same way. More particularly, chlorides have been synthesized by replacing hydrofluoric acid gas with the corresponding gaseous halo-hydric acid and consequently, in the catalyst, the fluoride with the corresponding halogenide. Everything else being equal, this simple modification makes it possible to obtain the desired halide. It is preferable to use a compound of the formula (I) which has on the carbonic carbon the desired halide or one whose atomic number is higher. In the contrary case, it is advisable to work in the top regions of the halo-hydric acid/substrate molar ratios.

The following examples illustrate the invention. However, the invention is not limited to these examples.

EXAMPLES 1 TO 2

CHROMIUM OXIDE CATALYST

Example 1

A stream of vaporized phenyl chloroformate (0.21 mmol/min) was mixed with gaseous hydrofluoric acid at a temperature of 300° C., to give a reaction mixture containing 48 moles of hydrofluoric acid per mole of phenyl chloroformate.

This mixture was passed through a tubular reactor made of Hastelloy C 276, 35 cm in length and 2.0 cm in internal diameter. The reactor was filled with chromium catalyst. The catalyst was prepared according to M. Garnier, Bull. Soc. Chim. Fr. 1984 No. 3–4, p. 91 to 96 herein incorporated by reference.

The temperature of the catalyst bed was maintained at 400° C. and the contact time $T_f$ was 2 gxs/cm$^3$.

The gaseous products were condensed, diluted in water, neutralized with aqueous sodium hydroxide (NaOH) and extracted with dichloromethane.

The solution in dichloromethane was analyzed by vapor phase chromatography, nuclear magnetic resonance and mass spectrometry.

The fluorobenzene yield was 70%.

Example 2

The procedure of Example 1 was repeated except that the chromium catalyst was replaced with a chromium oxide catalyst on alumina (Harshan R 010T 1/8). The catalyst was pretreated with hydrofluoric acid. The HF/chloroformate molar ratio was 100 and the contact time $T_f$ was 0.4 gxs/cm$^3$.

The fluorobenzene yield was 50%.

EXAMPLES 3 TO 5

METAL CATALYST

Example 3

A stream of vaporized phenyl chloroformate (0.25 mmol/min) was mixed with gaseous hydrofluoric acid at a temperature of 400° C. to give a reaction mixture containing 47 moles of hydrofluoric acid per mole of phenyl chlorofor-mate. This mixture was passed through a tubular reactor made of Hastelloy C 276, 35 cm in length and 2.0 m in internal diameter. The reactor was filled with 4 mm diameter steel balls.

The temperature of the catalyst bed was maintained at 400° C. and the contact time $T_f$ was 8.4 gxs/cm$^3$. The gaseous reaction products were condensed, diluted in water, neutralized with aqueous sodium hydroxide and extracted with dichloromethane. The solution in dichloromethane was analyzed by vapor phase chromatography, nuclear magnetic resonance and mass spectrometry. The fluorobenzene yield was 81%.

Example 4

The procedure of Example 1 was repeated except that the phenyl chloroformate was replaced with phenyl fluorofor-mate. the HF/phenyl fluoroformate ratio was 61 with a contact time $T_f$ of 3.8 gxs/cm$^3$.

The fluorobenzene yield was 15%.

Example 5

The procedure of Example 1 was repeated in a reactor filled with Hastelloy C 276 balls instead of steel balls.

The fluorobenzene yield was 0.8%.

Example 6

1-CHLORO-4-FLUOROBENZENE

A stream of vaporized phenyl 4-chlorochloroformate (0.22 mmol/min) was mixed with gaseous hydrofluoric acid at a temperature of 307° C. to give a reaction mixture containing 132 moles of hydrofluoric acid per mole of phenyl 4-chlorochloroformate.

This mixture was passed through a tubular reactor made of Hastelloy C 276, 35 cm in length and 2.0 cm in internal diameter. The reactor contained 10 g of aluminum fluoride beads.

The temperature of the catalyst bed was maintained at 307° C. and the contact time $T_f$ was 0.47 gxs/cm$^3$.

The stream leaving the reactor was collected in a 1-liter receiver pot which contained 100 ml of dichloromethane and 750 ml of water.

The flow of the gaseous mixture was stopped after 71 minutes.

The received material was extracted with dichloromethane and the organic phase was washed with water, dried and neutralized over potassium fluoride, filtered, and analyzed by vapor phase chromatography, nuclear magnetic resonance and mass spectrometry.

The 1-chloro-4-fluorobenzene yield was 55%.

Example 7

3-FLUOROTOLUENE

A stream of vaporized phenyl 3-methylchloroformate (0.43 mmol/min) was mixed with gaseous hydrofluoric acid at a temperature of 307° C. to give a reaction mixture containing 18 moles of hydrofluoric acid per mole of phenyl 3-methylchloroformate.

This mixture was passed thorugh a tubular reactor made of Hastelloy C 276, 35 cm in length and 2.0 cm in internal diameter. The reactor contained 10 g of aluminum fluoride beads.

The temperature of the catalyst bed was maintained at 307° C. and the contact time $T_f$ was 0.8 gxs/cm$^3$. The stream leaving the reactor was collected in a 1-liter receiver pot which contained 100 ml of dichloromethane and 750 ml of water.

The flow of the gaseous mixture was stopped after 2 hours and 14 minutes.

The received material was extracted with dichloromethane and the organic phase was washed with water, dried and neutralized over potassium fluoride, filtered and analyzed by vapor phase chromotography, nuclear magnetic resonance and mass spectrometry.

The 3-fluorotoluene yield was 95%.

Example 8

1-FLUORONAPHTHALENE

A stream of vaporized 1-naphthyl chloroformate (0.23 mmol/min) was mixed with gaseous hydrofluoric acid at a temperature of 409° C. to give a reaction mixture containing 83 moles of hydrofluoric acid per mole of 1-naphthyl chloroformate.

This mixture was passed through a tubular reactor made of Hastelloy C 276, 35 cm in length and 2.0 cm in internal diameter. The reactor contained 10 g of 2 mm diameter aluminum fluoride beads.

The temperature of the catalyst bed was maintained at 409° C. and the contact time $T_f$ was 0.6 gxs/cm$^3$.

The stream leaving the reactor was collected in a 1-liter receiver pot which contained 100 ml of dichloromethane and 750 ml of water.

The flow of the gaseous mixture was stopped after 72 minutes.

The material received was extracted with dichloromethane and the organic phase was washed with water, dried and neutralized over potassium fluoride, filtered and analyzed by vapor phase chromatography, nuclear magnetic resonance and mass spectrometry.

The 1-fluoronaphthalene yield was 81%.

Example 9

1,4-DIFLUOROBENZENE

A stream of vaporized phenyl 4-fluorochloroformate (0.30 mmol/min.) was mixed with gaseous hydrofluoric acid at a temperature of 407° C. to give a reaction mixture containing 94 moles of hydrofluoric acid per mole of phenyl 4-fluorochloroformate.

This mixture was passed through a tubular reactor made of Hastelloy C 276, 35 cm in length and 2.0 cm in internal diameter. The reactor contained 10 g of aluminum fluoride beads.

The temperature of the catalyst bed was maintained at 407° C. and the contact time $T_f$ was 0.42 gxs/cm$^3$.

The stream leaving the reactor was collected in a 1-liter receiver pot which contained 100 ml of dichloromethane and 750 ml of water.

The flow of the gaseous mixture was stopped after 60 minutes. The material received was extracted with dichloromethane and the organic phase was washed with water, dried and neutralized over potassium fluoride, filtered, and analyzed by vapor phase chromatography, nuclear magnetic resonance and mass spectrometry. The 1,4-difluorobenzene yield was 96%.

Example 10

4-FLUOROMETHOXYBENZENE

A stream of vaporized phenyl 4-methoxychloroformate (0.23 mmol/min) was mixed with gaseous hydrofluoric acid at a temperature of 407° C. to give a reaction mixture containing 40 moles of hydrofluoric acid per mole of phenyl 4-methoxychloroformate.

This mixture was passed through a tubular reactor made of Hastelloy C 276, 35 cm in length and 2.0 cm in internal diameter. The reactor contained 10 g of aluminum fluoride beads.

The temperature of the catalyst bed was maintained at 407° C. and the contact time $T_f$ was 1.25 gxs/cm$^3$.

The stream leaving the reactor was collected in a 1-liter receiver pot which contained 100 ml of dichloromethane and 750 ml of water.

The flow of the gaseous mixture was stopped after 2 hours and 24 minutes.

The material received was extracted with dichloromethane and the organic phase was washed with water, dried and neutralized over potassium fluoride, filtered, and analyzed by vapor phase chromatography, nuclear magnetic resonance and mass spectrometry.

The 4-fluoromethoxybenzene yield was 5%, and the yield of 4-fluorophenol was 18%.

Example 11

2-FLUOROBIPHENYL

A stream of vaporized phenyl 2-phenylchloroformate (0.17 mmol/min) was mixed with gaseous hydrofluoric acid at a temperature of 356° C. to give a reaction mixture containing 224 moles of hydrofluoric acid per mole of phenyl 2-phenylchloroformate.

This mixture was passed through a tubular reactor made of Hastelloy C 276, 35 cm in length and 2.0 cm in internal diameter. The reactor contained 10 g of aluminum fluoride beads.

The temperature of the catalyst bed was maintained at 356° C. and the contact time $T_f$ was 0.42 gxs/cm$^3$.

The stream leaving the reactor was collected in a 1-liter receiver pot which contained 100 ml of dichloromethane and 750 ml of water.

The flow of the gaseous mixture was stopped after 60 minutes.

The material received was extracted with dichloromethane and the organic phase was washed with water, dried and neutralized over potassium fluoride, filtered, and analyzed by vapor phase chromatography, nuclear magnetic resonance and mass spectrometry.

The 2-fluorobiphenyl yield was 23%.

Example 12

1-BROMO-4-FLUOROBENZENE

A stream of vaporized phenyl 4-bromochloroformate (0.33 mmol/min) was mixed with gaseous hydrofluoric acid at a temperature of 407° C., to give a reaction mixture containing 76 moles of hydrofluoric acid per mole of phenyl 4-bromochloroformate.

This mixture was passed through a tubular reactor made of Hastelloy C 276, 35 cm in length and 2.0 cm in internal diameter. The reactor contained 10 g of aluminum fluoride beads.

The temperature of the catalyst bed was maintained at 407° C. and the contact time $T_f$ was 0.4 gxs/cm$^3$.

The stream leaving the reactor was collected in a 1-liter receiver pot which contained 100 ml of dichloromethane and 750 ml of water.

The flow of the gaseous mixture was stopped after 50 minutes.

The material received was extracted with dichloromethane and the organic phase was washed with water, dried and neutralized over potassium fluoride, filtered, and analyzed by vapor phase chromatography, nuclear magnetic resonance and mass spectrometry.

The 1-bromo-4-fluorobenzene yield was 70%.

Example 13

FLUOROBENZENE OVER TITANIUM OXIDE

A stream of vaporized phenyl chloroformate (0.25 mmol/min) was mixed with gaseous hydrofluoric acid at a temperature of 220° C. to give a reaction mixture containing 152 moles of hydrofluoric acid per mole of phenyl chloroformate.

This mixture was passed through a tubular reactor made of Hastelloy C 276, 35 cm in length and 2.0 cm in internal diameter. The reactor contained 10 g of titanium oxide prefluorinated with hydrofluoric acid at 220° C.

The temperature of the catalyst bed was maintained at 220° C. and the contact time $T_f$ was 0.44 gxs/cm$^3$.

The stream leaving the reactor was collected in a 1-liter receiver pot which contained 100 ml of dichloromethane and 750 ml of water.

The flow of the gaseous mixture was stopped after 50 minutes. The yield was 54% as set forth in Table V.

Example 14

Various Tests

Additional tests were carried out using the same procedure as set forth in Example 1. The results of these tests are summarized in the following tables.

TABLE I

| CATALYSIS USING ALLOY | | | |
| --- | --- | --- | --- |
| STARTING MATERIAL | CATALYST | TEMPERATURE | YIELD BASED ON THE STARTING MATERIAL |
| PhOCOCl | Stainless Steel | 290° C. | 0.5% |
| " | Stainless Steel | 400° C. | 80% |
| " | Hastelloy C 276 | 400° C. | 0.8% |
| " | Iron | 400° C. | 0.5% |
| " | Hastelloy | 500° C. | 2.5% |
| PhOCOF | Stainless Steel | 400° C. | 26% |

TABLE II

CATALYSIS USING METAL OXIDE

| STARTING MATERIAL | CATALYST | TEMPERATURE | YIELD BASED ON THE STARTING MATERIAL |
|---|---|---|---|
| PhOCOCl | CATA TFA | 300° C. | 18% |
| " | $Cr_2O_3$ analyt. reagent $CR_2O_3$ | 300° C. | 7% |
| " | $Al_2O_3$ + MgO | 300° C. | 50% |
| " | $CrCl_3.6H_2O$ | 500° C. | 25% |
| PhOCOOPh | $Al_2O_3 + Cr_2O_3$ MgO | 300° C. | 15% |

Example 15

Comparative Test Decomposition of Ph—OCO—F

Made from the European Patent application published under the number 011 8241.

The procedure of the previous examples was carried out using the following parameters:

Temperature: 350° C.
Rate of inert gas (nitrogen): 60 l/h
Substrate rate: 50 mmol/h (6 ml/h).
The contact time: 0.2 g s/ml
The results obtained are set forth in the following table.

TABLE III

| USE DURATION OF THE CATALYST | 1 hour | 2 hours | 4 hours | 5 hours | 6 hours |
|---|---|---|---|---|---|
| YIELD/INITIAL PRODUCT | 62% | 53% | 19% | 9% | 7% |

The catalyst was poisoned after only 4 hours. There was also production of tar and heavy products.

Example 16

Role of Hydrohalic Acid

The procedure of the previous examples was followed for various catalyst types in the absence of hydrohalic acid. The following parameters were used:

Temperature: 350° C.
Inert gas rate (nitrogen): 40 l/h.
Contact time: 0.5 g s/ml The results were obtained after 1 hour to ensure that the equilibrium was reached. These results are set forth in the following table:

TABLE IV

| CATALYST | $CeF_3$ | $TiO_2$ | $ZrO_2$ | $Cr_2O_3$ |
|---|---|---|---|---|
| YIELD | 3% | 0% | 0% | 4% |

Example 17

Duration Test

The procedure of the previous examples was followed using the following parameters:

Temperature: 400° C.
Contact time: 0.5 g s/ml
HF-substrate ratio: 70:1

The substrate was metacresyl chloroformate (to obtain metafluorotoluene). The catalyst was 10 g of gamma alumina fluorinated during 2 hours under the reaction condition but without substrate.

The fact that the gaseous mixture issuing from the reactor is identical to the feed was verified. The regeneration was accomplished by feeding air into the reactor at 450° C. for a period of 3 hours with a flow rate of 4 l/hr. The results obtained are set forth in FIG. 1.

The yields were calculated with respect to initial product. Drastic diminution in yield would have resulted but for the ability to regenerate the catalyst. The above examples demonstrate preferred embodiments. Various modifications which would occur to one of ordinary skill in the art are included within the scope of the invention.

TABLE V

EXPLORATION OF THE DOMAIN

| SUBSTRATE | CATALYST | TEMPERATURE ° C. | HF/SUBSTRATE RATIO (molar) | Tf g s/ml | FLUORINE YIELD |
|---|---|---|---|---|---|
| | TRANSITION METALS | | | | Flourobenzene |
| PhOCOCl | Stainless steel 316 L | 290 | 67 | 2 | 0.5% |
| PhOCOCl | " | 400 | 47 | 8 | 80% |
| PhOCOF | " | 400 | 11 | 6 | 26% |
| PhOCOCl | HASTELLOY C 276 | 400 | 30 | 80 | 0.8% |
| PhOCOCl | HASTELLOY | 500 | 74 | 3.7 | 2.5% |
| PhOCOCl | $Cr_2O_3$ Amorphous powder | 300 | 50 | 2 | 70% |
| PhOCOCl | $Cr_2O_3$ analyt. reag. | 300 | 112 | 0.5 | 2.5% |
| PhOCOCl | $Cr_2O_3 + Al_2O_3$ Harshaw | 300 | 100 | 0.4 | 50% |
| PhOCOPh | $Cr_2O_3 + Al_2O_3$ Harshaw | 300 | 367 | 0.4 | 15% |
| PhOCOCl | Iron | 400 | 85 | 1 | 0.5% |
| PhOCOCl | Alumina* | 300 | 56 | 0.8 | 90% |
| $CH_3$—PhOCOCl | " | 300 | 56 | 0.8 | >95% fluorotoluene |
| PhOCOCl | Alumina | 300 | 18 | 1.2 | 80% fluorobenzene |
| PhOCOF | Gamma alumina | 300 | 71 | 0.7 | 99% fluorobenzene |

TABLE V-continued

EXPLORATION OF THE DOMAIN

| SUBSTRATE | CATALYST | TEMPERATURE ° C. | HF/SUBSTRATE RATIO (molar) | Tf g s/ml | FLUORINE YIELD |
|---|---|---|---|---|---|
| m-Me—PhOCOCl | " | 300 | 84 | 0.8 | 95% m-fluorotoluene |
| PhOCOCl | $AlF_3$ | 300 | 40 | 1.5 | 90% fluorobenzene |
| PhOCOCl | $TiO_2$ | 300 | 80 | 0.4 | 23% |
| PhOCOCl | " | 300 | 29 | 2 | 60% |
| PhOCOCl | ZnO | 300 | 238 | 0.2 | 7% |
| PhOCOCl | $ZrO_2$ | 300 | 136 | 0.4 | 46% |
| PhOCOCl | ZnO | 300 | 18 | 12 | 14% |
| PhOCOCl | $TiO_2$ | 220 | 152 | 0.4 | 54% |
| PhOCOCl | $LaF_3$ | 300 | 32 | 1.2 | 41% |
| PhOCOCl | " | 400 | 59 | 0.6 | >78% |
| PhOCOCl | $CeF_3$ | 300 | 81 | 0.5 | 32% |
| PhOCOCl | $MgF_2$ | 400 | 51 | 0.7 | 14% |
| Alpha-naphthyl chloroformate | Gamma alumina | 400 | 124 | 0.5 | 1-Fluoronaphthalene 92% |
| p-Me—O—PhOCOCl | " | 400 | 40 | 0.23 | p-Fluorophenol 18% p-Fluoroanisole 5% |
| p-Bromo-PhOCOCl | Gamma alumina | 400 | 76 | 0.4 | p-Bromofluorobenzene 70% |
| p-Fluoro-PhOCOCl | Gamma alumina | 400 | 94 | 0.3 | p-Difluorobenzene 96% |
| o-Phenyl-PhOCOCl | Gamma alumina | 300 | 150 | 0.5 | 2-Fluorobiphenyl 24% |
| PhOCSCl | Gamma alumina | 300 | 120 | 0.4 | Fluorobenzene 91% |
| m-Me—PhOCOCl | Gamma alumina | 250 | 89 | 0.6 | m-Fluorotoluene 40% |
| m-Me—PhOCOCl | Gamma alumina | 400 | 54 | 0.6 | m-Fluorotoluene 94% |
| $PhOCF_3$ | Gamma alumina | 400 | 88 | 0.4 | Fluorobenzene 50% |
| $PhOCCl_3$ | Gamma alumina | 400 | 36 | 1.2 | Fluorobenzene 23% |

*This is an alumina in the form of 2-mm diameter beads with a specific surface of 200 $m^2/g$.
NAME EXP SPHERALITE SPH 537

What is claimed is:

1. A process for the preparation of an aryl halide compound by attaching a halogen atom directly to the aromatic ring comprising the step of:

contacting a gaseous mixture containing a hydrohalic acid and at least one substrate compound selected from the group consisting of an aryl halogen formate, an aryl carbonate and an aryl compound having a radical of the formula

—O—CY—A wherein Y represents a chalcogen or two halogen atoms and A represents a halogen and wherein said substrate compound has no greater than 50 carbon atoms, with a Lewis acid catalyst at a temperature of at least between about 200° C. and about 800° C. for a contact time Tf of between about $10^{-3}$ and 100 g×s/cm³, said contact time being sufficient to obtain said aryl halide having a halogen atom bonded directly to the aromatic ring, wherein the ratio of hydrohalic acid to substrate compound is in excess of the stoichiometric quantity required to effect complete halogen exchange but not less than 5.

2. The process of claim 1, wherein said at least one substrate compound has the formula (II)

$(R_1)_n$—Ar—O—CY—A (II)

wherein

Ar represents an aromatic radical;

radical(s) $R_1$, which may be the same or different, represent: an electron attracting unit;

n represents the number of substituents and is equal to 0 or a whole number that is no greater than the number of substitutable positions on the aromatic ring.

3. The process of claim 2, wherein Y represents sulfur or oxygen.

4. The process of claim 3, wherein Y represents sulfur.

5. The process of claim 3, wherein Y represents oxygen.

6. The process of claim 2, wherein Y represents two of the same halogen atoms.

7. The process of claim 2, wherein Ar represents a monocyclic, polycyclic or heterocyclic aromatic radical.

8. The process claim 2, wherein $R_1$ represents a halogen.

9. The process of claim 2, wherein $R_1$ represents a nitro and/or cyano group.

10. The process of claim 2, wherein A represents —O—R'$_2$ and R'$_2$ is $(R1)_n$—Ar—.

11. A process for the preparation of an aryl halide compound by attaching a halogen atom directly to the aromatic ring comprising the step of:

contacting a gaseous mixture containing a hydrohalic acid and at least one substrate compound of the formula $(R_1)_n$—Ar—O—CY—A wherein Y represents a chalcogen or two halogen atoms;

Ar represents a phenyl radical;

radicals ($R_1$), which may the same or different, represent an electron attracting unit and n is less than or equal to 5; and A represents a halogen with a Lewis acid catalyst at a temperature of at least between about 200° C. and about 800° C. for a contact time Tf of between about $10^{-3}$ and 100 gxs/cm$^3$, said contact time being sufficient to obtain said aryl halide having a halogen atom bonded directly to the aromatic ring, wherein the ratio of hydrohalic acid to substrate compound is in excess of the stoichiometric quantity required to effect complete halogen exchange but not less than 5.

12. The process of claim 1, wherein the molar ratio of hydrohalic acid to the substrate compound is at least equal to 1:1.

13. The process of claim 12, wherein said molar ratio is between 10:1 and 1,000:1.

14. A process for the preparation of an aryl halide compound by attaching a halogen atom directly to the aromatic ring comprising the step of:

contacting a gaseous mixture containing a hydrohalic acid with a chloroformate substrate compound with a Lewis acid catalyst at a temperature of at least between about 200° C. and about 800° C. for a contact time Tf of between about $10^{-3}$ and 100 gxs/cm$^3$, said contact time being sufficient to obtain said aryl halide having a halogen atom bonded directly to the aromatic ring, wherein the ratio of hydrohalic acid to substrate compound is in excess of the stoichiometric quantity required to effect complete halogen exchange but not less than 5.

15. The process of claim 1, wherein the temperature of contacting is between about 300° and about 500° C.

16. The process of claim 1, wherein the gaseous mixture is at a total pressure of between $10^{-2}$ MPa and 20 MPa.

17. The process of claim 1, wherein the gaseous mixture further comprises a gas which is inert.

18. The process of claim 1, wherein said Lewis acid catalyst contains at least one chemical species selected from the group consisting of the transition elements, and silicon, and wherein the Lewis acid catalyst is in the form of chalcogenide, halide, alloys and mixtures thereof.

19. The process of claim 18, wherein the transition elements are selected from the group consisting of metallic elements of Groups III, IVb and Vb.

20. The process of claim 19, wherein the elements of Group III are selected from the group consisting of chromium, germanium and antimony.

21. The process of claim 19, wherein the elements of Group III are selected from the group consisting of actinium, thorium and uranium.

22. The process of claim 18, wherein the form of the Lewis acid catalyst is an alloy.

23. The process as claimed in claim 18, wherein said chemical species is selected from the group consisting of chromium, aluminum and antimony fluorides and oxyfluorides and mixtures thereof.

24. The process of claim 1, wherein said at least one substrate compound has the formula (II)

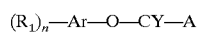

wherein

Ar represents an aromatic radical;

radical(s) $R_1$, which may be the same or different, represent: a —Z—$R_2$ group, in which Z may be a single bond, an oxygen atom, a sulfur atom, or the groups —N$R_3$—, —CO—, —OCO—, —COO—, —SO—, —SO$_2$—, or —SO$_3$—;

$R_2$ represents a hydrogen atom or an alkyl, an acyl or an aryl radical having at least 8 carbon atoms, and where $R_3$ may be of the same type as $R_2$ or form a nitrogenous heterocycle with $R_2$ and the nitrogen atom that carries it;

n represents the number of substituents and is equal to 0 or a whole number that is no greater than the number of substitutable positions on the aromatic ring.

25. The process of claim 24, wherein Y represents sulfur or oxygen.

26. The process of claim 25, wherein Y represents sulfur.

27. The process of claim 25, wherein Y represents oxygen.

28. The process of claim 24, wherein Y represents two of the same halogen atoms.

29. The process of claim 24, wherein Ar represents a monocyclic, polycyclic or heterocyclic aromatic radical.

30. The process of claim 24, wherein A represents —O—R'$_2$— and R'$_2$ is ($R_1$)—Ar—.

31. The process of claim 24, wherein Ar denotes a phenyl radical and n is less than or equal to 5.

32. A process for the preparation of an aryl halide compound by attaching a halogen atom directly to the aromatic ring comprising the step of:

contacting a gaseous mixture containing a hydrohalic acid and at least one substrate compound selected from the group consisting of an aryl halogen formate, an aryl carbonate, and an aryl compound having a radical of the formula

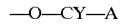

wherein Y represents a chalcogen or two halogen atoms and A represents a halogen and wherein said substrate compound has no greater than 50 carbon atoms, with a Lewis acid catalyst at a temperature of between about 200° C. and about 800° C.;

wherein the contact time ($T_f$) is between about $10^{-3}$ and 100 gxs/cm$^3$, and said contact time is sufficient for removing the —O—CY—A substituent from the substrate compound and bonding a halogen atom from the hydrohalic acid directly to the aromatic ring to obtain said aryl halide having a halogen atom bonded directly to the aromatic ring.

* * * * *